US006517849B1

(12) United States Patent
Seger et al.

(10) Patent No.: US 6,517,849 B1
(45) Date of Patent: Feb. 11, 2003

(54) TISSUE PRODUCTS CONTAINING ANTIVIRAL AGENTS WHICH ARE MILD TO THE SKIN

(75) Inventors: Geoffrey Eugene Seger, Tunkhannock, PA (US); Kimberly Ann Biedermann, Cincinnati, OH (US); Kamilah Apewaiye Gbadamosi, Cincinnati, OH (US); Stephen Robert Kelly, Owenton, KY (US); Paul Thomas Weisman, Cincinnnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/659,893

(22) Filed: Sep. 12, 2000

Related U.S. Application Data

(63) Continuation-in-part of application No. 09/643,903, filed on Aug. 21, 2000, now abandoned, and a continuation-in-part of application No. 09/421,131, filed on Oct. 19, 1999, now abandoned, and a continuation-in-part of application No. 09/420,646, filed on Oct. 19, 1999, now abandoned, and a continuation-in-part of application No. 09/421,084, filed on Oct. 19, 1999, now Pat. No. 6,294,186, and a continuation-in-part of application No. 09/458,750, filed on Dec. 10, 1999, now abandoned, which is a continuation-in-part of application No. 09/421,179, filed on Oct. 19, 1999, now abandoned

(60) Provisional application No. 60/214,340, filed on Jun. 27, 2000.

(51) Int. Cl.$^7$ .............................................. A01N 25/34
(52) U.S. Cl. ...................... 424/402; 424/404; 424/443; 424/78.08; 424/78.24; 424/630; 424/637; 424/642; 424/646; 424/647; 424/648
(58) Field of Search ................................ 424/402, 443, 424/404, 78.08, 78.24, 630, 637, 642, 646, 647, 648

(56) References Cited

U.S. PATENT DOCUMENTS

| | | | |
|---|---|---|---|
| 3,046,196 A | 7/1962 | de Vaulchier | 167/65 |
| 3,138,533 A | 6/1964 | Heim et al. | 167/84 |
| 3,227,614 A | 1/1966 | Scheuer | 167/84 |
| 3,374,097 A | 3/1968 | Deerfield, III | 99/86 |
| 3,817,702 A | 6/1974 | Paulus et al. | 8/120 |
| 3,867,300 A | 2/1975 | Karabinos et al. | 252/106 |
| 4,045,364 A | 8/1977 | Richter | 252/106 |
| 4,355,021 A | 10/1982 | Mahl et al. | 424/28 |
| 4,732,797 A | 3/1988 | Johnson et al. | 428/74 |
| 4,738,847 A | 4/1988 | Rothe et al. | 424/443 |
| 4,764,418 A | 8/1988 | Kuenn et al. | 428/284 |
| 4,767,788 A | 8/1988 | Diana | 514/574 |
| 4,824,689 A | 4/1989 | Kuenn et al. | 427/2 |
| 4,828,912 A | 5/1989 | Hossain et al. | 428/289 |
| 4,897,304 A | 1/1990 | Hossain et al. | 428/289 |
| 4,975,217 A | 12/1990 | Brown-Skrobot et al. | 252/107 |
| 5,143,773 A | 9/1992 | Takuno | 428/137 |
| 5,334,388 A | 8/1994 | Hoang et al. | |
| 5,539,088 A | 7/1996 | Schumacher et al. | 534/633 |
| 5,595,754 A | 1/1997 | Ito et al. | 424/443 |
| 5,607,754 A | 3/1997 | Giles et al. | 428/211 |
| 5,871,763 A | 2/1999 | Luu et al. | 424/402 |
| 5,905,062 A | 5/1999 | Elliott et al. | 510/124 |
| 5,906,814 A | 5/1999 | Epstein | |
| 5,935,384 A | 8/1999 | Taniguchi | 162/172 |
| 5,968,853 A | 10/1999 | Kelly et al. | 442/85 |
| 6,238,682 B1 * | 5/2001 | Klofta et al. | 424/402 |

FOREIGN PATENT DOCUMENTS

| | | |
|---|---|---|
| EP | 0926299 A2 | 6/1999 |
| FR | 2538238 A1 | 6/1984 |
| GB | 2134781 A | 8/1984 |
| JP | 63-305872 | 12/1988 |
| JP | 01 022804 A | 1/1989 |
| JP | 07-157415 | 6/1995 |
| JP | 07 189170 A | 7/1995 |
| JP | 10 057268 A | 3/1998 |
| SE | 466 111 B | 12/1991 |

OTHER PUBLICATIONS

Humectants and skin moisturizing—recent advances, Fragrance Journal, (14), 43–54, (1975), Tatsuya Ozawa.
Japanese Industrial Standard, JIS P 4501—1993.
Nature of Cosmetic Films on the Skin, J. Soc. Cosmetic Chemists—Mar. 4, 1967.
Skin Moisturizers. II. The Effects of Cosmetic Ingredients on Human Stratum Corneum, J. Soc. Cosmetic Chemists—May 1974.
Identification of a Natural Moisturizing Agent in Skin, J. Soc. Cosmetic Chemists—May 27, 1967.
Factors Which Influence The Water Content Of The Stratum Corneum, Department of Dermatology, Harvard University, and the Dermatological Laboratories, Massachusetts General Hospital.
Effect Of A Skin Cream Containing The Sodium Salt Of Pyrollidone Carboxylic Acid On Dry And Flaky Skin, J. Soc. Cosmetic Chemists—1978.
Torsional Measurements On Skin, J. Soc. Cosmetic Chemists—May 27, 1970.
Relation Of Dew Point And Barometric Pressure To Chapping Of Normal Skin.

* cited by examiner

Primary Examiner—Thurman K. Page
Assistant Examiner—Liliana Di Nola-Baron
(74) Attorney, Agent, or Firm—Julia A. Glazer; David K. Mattheis; David K. Weirich

(57) ABSTRACT

This application relates to antiviral tissue paper comprising pyrrolidone carboxylic acid as an antiviral agent. When added to tissue paper pyrrolidone carboxylic acid has the ability to kill certain strains of viruses which come into contact with the tissue. In addition to its antiviral efficacy, pyrrolidone carboxylic acid tends to be mild to the skin thus mitigating the potential for skin irritation. Furthermore, upon transfer to the skin, pyrrolidone carboxylic acid assists in retention of the natural moisture of the skin while continuing to kill deleterious viruses.

35 Claims, No Drawings

TISSUE PRODUCTS CONTAINING ANTIVIRAL AGENTS WHICH ARE MILD TO THE SKIN

CROSS REFERENCES TO RELATED APPLICATIONS

This application claims the benefit of and is a continuation-in-part U.S. Ser. No. 09/643,903 filed on Aug. 21, 2000 now abandoned; which claims priority to U.S. Provisional Application No. 60/214,340 filed Jun. 27, 2000; U.S. Ser. No. 09/421,131 filed Oct. 19, 1999 now abandoned; U.S. Ser. No. 09/420,646 filed Oct0. 19, 1999, now abandoned; U.S. Ser. No. 09/421,084 filed Oct. 19, 1999 U.S. Pat. No. 6,294,486; and U.S. Ser. No. 09/458,750 filed Dec. 10, 1999 now abandoned, which is a continuation-in-part of U.S. Ser. No. 09/421,179 filed Oct. 19, 1999, now abandoned.

TECHNICAL FIELD

This application relates to antiviral tissue paper comprising pyrrolidone carboxylic acid. When added to tissue paper pyrrolidone carboxylic acid has the ability to kill certain strains of viruses which come into contact with the tissue. In addition to its antiviral efficacy, pyrrolidone carboxylic acid is mild to the skin thus mitigating the potential for skin irritation. This application further relates to antiviral lotions comprising pyrrolidone carboxylic acid. A process for making the antiviral tissue paper of this invention is also disclosed.

BACKGROUND OF THE INVENTION

Whether it be a household, workplace, educational facility or any other location where people tend to gather, preventing the spread of germs is a difficult but yet desirable task. For instance, it is well documented that many hours of productive work are lost due to individuals becoming infected with the common cold or influenza virus.

When one suffers from the common cold or influenza virus, one's mucus is the source of a very high concentration of viruses. After the mucus is aerosolized by a sneeze, cough, or other environmental surfaces, the virus within the mucus has the potential to infect other individuals coming into contact with it. Likewise, mucus deposited into a facial tissue also has the potential to infect others if they come in contact with the contaminated tissue. Transfer of this mucus on the tissue to another individual will likely be through accidental or unintentional contact.

As an example of a possible transfer scenario, consider a cold sufferer who accidentally leaves a mucus infected facial tissue on a hard surface of some type. This hard surface might be a kitchen countertop, a bathroom vanity surface, an office desk or some other piece of furniture. Another family member or colleague may accidentally come into contact with the infected mucus after picking up the tissue to throw it away or by contacting the contaminated countertop area. After coming into such contact with the mucus on the tissue, it is very possible for that individual to become infected with the viral condition (i.e., common cold, influenza) especially if the infected mucus comes into contact with that individual's mucosal membranes.

Another transmission scenario is through the disposal of the facial tissues contaminated with the virus containing mucus. After a household waste basket becomes filled with trash containing a high concentration of infected tissues, it obviously needs to be disposed of in some manner. During this transfer of the household trash into another larger disposal unit, the individual transferring the trash may come into contact with the contaminated tissue. Once again, this individual is at a higher risk for contracting the virus. Many other potential modes of virus transmission are possible after the facial tissue has become infected with the mucus.

Furthermore, virus transmission is not the only concern when one has a cold. As is well known, cold and influenza sufferers typically have sore and irritated skin regions associated with the nose and lips. The irritation, inflammation and redness around the nose and lips can have several causes. A prime one is, of course, the sheer necessity of frequently blowing one's nose into he tissue, and wiping the resultant nasal discharge from the nose and surrounding area.

The degree of irritation and inflammation caused by such blowing and wiping is directly proportional to: (1) the surface roughness of the tissue used; (2) the number of times the nose and its surrounding areas are in contact with the tissue; and (3) the irritation potential of any additives applied to the tissue paper. It is thus imperative to use antiviral compositions that are as mild as possible.

U.S. Pat. No. 4,738,847 issued to Rothe et al. on Apr. 19, 1988 purports to teach a three ply cellulosic tissue wherein a virucidal composition is substantially confined to the center ply. The virucidal composition is composed of citric acid and/or malic acid. A surfactant, sodium lauryl sulfate, may also be included.

U.S. Pat. No. 4,828,912 issued to Hossain et al. on May 9, 1989 purports to teach a virucidal composition applied to a tissue. The virucidal composition may include citric, malic, succinic, and/or benzoic acid. A surfactant may also be included.

Both of these suffer from the same drawback. The virucidal compositions are not mild to the skin.

The antiviral agent(s) of the present invention is effective at killing certain strains of viruses such as influenza virus and rhinovirus. Furthermore, it is very mild to the skin. Additionally, it provides a unique residual effect where upon transfer from the tissue to the user, the antiviral agent can potentially protect those skin regions which come in contact with the viral infections. Furthermore, because the antiviral agent tends to be mild, the potential for skin irritation and stinging in these areas is greatly reduced. As the potential for skin irritation and stinging is reduced, the antiviral agent may be placed on the outer plies of the tissue product whereby it can easily be transferred directly to the skin. Yet further, this allows for more immediate contact of the antiviral agent with the mucosal discharge. Hence, the antiviral agent does not have to be confined to the inner plies of the tissue.

Yet further, the antiviral agent of the present invention tends to promote retention of the skin's natural moisture. With regard to retention of the skin's natural moisture there is much described in cosmetics literature that directly correlates skin health with moisture content of the stratum corneum (I. H. Blank, J. Invest. Dermatol., 18, 433 (1952); L. F. Gaul et al., J. Invest. Dermatol., 19, 9 (1952); O. K. Jacobi, J. Soc. Cosmet. Chem., 18, 149 (1967)).

The factors controlling skin moisture content comprise water soluble materials called Natural Moisturizing Factors (hereinafter referred to as "NMF") (O. K. Jacobi, J. Soc. Cosmet. Chem., 18, 149 (1967)); H. W. Spier et al., Hautarzt, 7, 2 (1956)); and lipids of the skin surface.

As the name denotes, NMF is found naturally in human skin primarily in the stratum corneum. The composition of NMF as documented by Spier et al. (Hautarzt, 7, 2, 1956), is a variety of free amino acids; lactates; urea; pyrrolidone carboxylic acid and the corresponding salts; and other organic derivatives and mineral salts.

Effects of the NMF constituents have been studied extensively for skin moisturization transepidermal water loss; and skin elasticity (Reiger, M., J. Soc. Cosmetic Chem., 35, 253 (1974)).

Although the mode of action has not been entirely elucidated, Laden et al. (J. Soc. Cosmetic Chem., 18, 351, (1967)) has determined that pyrrolidone carboxylic acid and its corresponding sodium salt are important components for skin moisturization and improving skin suppleness (Laden et al., J. Soc. Cosmetic Chem., 21, 417 (1970)).

This has been further supported by Clar et al. (International Journal of Cosmetic Science, 3, 101, (1981)) and Middleton et al. (J. Soc. Cosmetic Chem., 29, 201, (1978)) where creams and lotions containing pyrrolidone carboxylic acid and sodium pyrrolidone carboxylate are reported to improve skin hydration and reduce dry flaky skin. Other components in NMF such as lactate also improve water retention of the epidermis to a lesser extent than pyrrolidone carboxylic acid.

Hence, the present invention provides a surprising combination of unique properties including immediate and residual antiviral efficacy, mildness, and the potential to assist with the retention of the skin's natural moisture.

The benefits of utilizing the tissue product of the present invention include a tissue product that is effective at preventing the spread of certain cold and flu viruses while being comfortable to use and potentially providing additional skin benefits to the user.

SUMMARY OF THE INVENTION

The present invention relates to antiviral tissues that are mild to the skin. The antiviral tissue product comprises one or more fibrous ply(ies) and an antiviral composition. The antiviral composition comprises pyrrolidone carboxylic acid. The pyrrolidone carboxylic acid may comprise from about 0.05% to 50% by weight of the antiviral tissue product. The antiviral composition may further comprise a metal salt. It may also include a surfactant. An optional organic acid may also be added. The antiviral tissue product may also contain a wet strength resin.

The antiviral tissue product may also include a lotion. The lotion may comprise polysiloxane. The lotion may also include an antiviral composition such as pyrrolidone carboxylic acid, citric acid, malic acid, lactic acid, glutaric acid, succinic acid, or mixtures thereof.

The antiviral tissue may optionally include a moisture barrier. The moisture barrier may include an antiviral composition.

The antiviral tissue product may have an "Easiness to Loosen in Water" test value of greater than about 100 seconds.

The present invention also relates to a process for making an antiviral tissue product.

DETAILED DESCRIPTION OF THE INVENTION

As used herein, the term "comprising" means that the various components, ingredients, or steps, can be conjointly employed in practicing the present invention. Accordingly, the term "comprising" encompasses the more restrictive terms "consisting essentially of" and "consisting of."

As used herein, "pyrrolidone carboxylic acid" collectively refers to its stereoisomers and tautomers.

As used herein, "moisture barrier" refers to a means for inhibiting the penetration of moisture through tissue. Suitable moisture barriers are disclosed in commonly assigned U.S. Pat. No. 5,968,853 issued to Kelly et al. on Oct. 19, 1999, U.S. Ser. No. 09/120,828 filed Jul. 22, 1998, now abandoned, and U.S. Pat. No. 6,132,803, filed Apr. 7, 1999, the disclosures of which are incorporated herein by reference.

As used herein, "antiviral agent" refers to something capable of killing viruses such as rhinovirus and influenza.

As used herein, "antiviral composition" refers to a composition which includes one or more antiviral agents.

As used herein, the terms "tissue paper web", "paper web", "web", "paper sheet", "tissue product", and "paper product" all refer to sheets of paper made by a process comprising the steps of forming an aqueous papermaking furnish, depositing this furnish on a foraminous surface, such as a fourdrinier wire, and removing the water from the furnish as by gravity or vacuum-assisted drainage, with or without pressing, and by evaporation.

As used herein the term "multi-ply tissue paper product" refers to a tissue paper comprised of at least two plies. Each individual ply in turn can be comprised of single-layered or multi-layered (stratified) tissue paper webs. The multi-ply structures are formed by bonding together two or more tissue webs such as by gluing or embossing.

As used herein, "carrier" refers to a means for delivering the antiviral composition to the tissue.

As used herein the terms "through air drying" and "blow through drying" refer to a technique of removing water from the web by drying the web with hot air.

As used herein, the terms "mechanical dewatering", "conventional wet pressing", and "conventional felt pressing" all refer to a technique of removing water from the web by mechanically pressing the web with a dewatering felt.

As used herein, the term "residual antiviral efficacy", refers to leaving a residue or imparting a condition on a keratinous tissue (e.g., skin) or other surfaces that remains effective and provides antiviral activity (against viruses such as rhinovirus) for some time after application.

Though the principle use of this invention is in connection with facial tissues, it is also applicable to other disposable paper products including but not limited to: bath tissue, table napkins, toweling, wipes, and other disposable articles and garments. The tissue paper of this invention may be conventionally wet pressed, through air dried, high bulk pattern densified, or high bulk, uncompacted tissue paper.

All percentages, ratios and proportions used herein are by weight unless otherwise specified.

A. Tissue Paper

The present invention is useful with tissue paper in general, including but not limited to conventionally felt-pressed tissue paper; high bulk pattern densified tissue paper; and high bulk, uncompacted tissue paper. It can be of a homogenous or multi-layered construction; and tissue paper products made therefrom can be of a single-ply or multi-ply construction. The tissue paper has a basis weight of between about 10 g/m$^2$ and 130 g/m$^2$, preferably between about 20 g/m$^2$ and 80 g/m$^2$, and most preferably between about 25 g/m$^2$ and 60 g/m$^2$. Unless otherwise specified, all amounts and weights relative to the paper are on a dry basis.

The tissue paper of the present invention comprises at least one fibrous ply and preferably two or more fibrous plies. The fibrous ply may be noncellulosic, preferably cellulosic, or a combination thereof. The fibrous ply may be layered. Each fibrous ply has two sides. Side one of the fibrous ply is oriented toward the user while side two of the fibrous ply is oriented away from the user. An antiviral composition made according to the present invention is applied to one or more of the fibrous plies. The antiviral composition may be applied to side one of the fibrous ply, side two of the fibrous ply, or both sides.

The antiviral composition may be applied uniformly or nonuniformly to the fibrous ply. It may be applied in a continuous pattern or a discontinuous pattern.

A lotion may be optionally applied to one or more of the fibrous plies. The lotion is preferably applied to side one of the fibrous ply. The lotion may optionally contain the antiviral composition of the present invention. A lotion may optionally be applied to one or more of the fibrous plies.

Conventionally pressed tissue paper and methods for making such paper are well known in the art. Such paper is typically made by depositing a papermaking furnish on a foraminous forming wire, often referred to in the art as a fourdrinier wire. Once the furnish is deposited on the forming wire, it is referred to as a web. The web is dewatered by pressing the web and drying at elevated temperature. The particular techniques and typical equipment for making webs according to the process just described are well known to those skilled in the art.

In a typical process, a low consistency pulp furnish is provided from a pressurized headbox. The headbox has an opening for delivering a thin deposit of pulp furnish onto the fourdrinier wire to form a wet web. The web is then typically dewatered to a fiber consistency of between about 7% and about 25% (total web weight basis) by vacuum dewatering and further dried by pressing operations wherein the web is subjected to pressure developed by opposing mechanical members, for example, cylindrical rolls.

The dewatered web is then further pressed and dried by a steam drum apparatus known in the art as a Yankee dryer. Pressure can be developed at the Yankee dryer by mechanical means such as an opposing cylindrical drum pressing against the web. Multiple Yankee dryer drums can be employed, whereby additional pressing is optionally incurred between the drums.

The tissue paper structures that are formed are referred to hereafter as conventional wet pressed tissue paper structures. Such sheets are considered to be compacted since the entire web is subjected to substantial mechanical compressional forces while the fibers are moist and are then dried while in a compressed state.

Pattern densified tissue paper is characterized by having a relatively high bulk field of relatively low fiber density and an array of densified zones of relatively high fiber density. The high bulk field is alternatively characterized as a field of pillow regions. The densified zones are alternatively referred to as knuckle regions. The densified zones can be discretely spaced within the high bulk field or can be interconnected, either fully or partially, within the high bulk field. The patterns can be formed in a non-ornamental configuration or can be formed so as to provide an ornamental design(s) in the tissue paper.

Preferred processes for making pattern densified tissue webs are disclosed in U.S. Pat. No. 3,301,746, issued to Sanford et al. on Jan. 31, 1967; U.S. Pat. No. 3,974,025, issued to Ayers on Aug. 10, 1976; U.S. Pat. No. 4,191,609, issued to Trokhan on Mar. 4, 1980; U.S. Pat. No. 4,637,859, issued to Trokhan on Jan. 20, 1987; U.S. Pat. No. 5,364,504, issued to Smurkoski et al. on Nov. 15, 1994; U.S. Pat. No. 5,366,785, issued to Sawdai on Nov. 22, 1994; U.S. Pat. No. 5,529,664, issued to Trokhan et al., on Jun. 25, 1996; U.S. Pat. No. 5,679,222, issued to Rasch et al., on Oct. 21, 1997; the disclosures of which are incorporated by reference.

In general, pattern densified webs are preferably prepared by depositing a papermaking furnish on a foraminous forming wire such as a fourdrinier wire to form a wet web and then juxtaposing the web against an array of supports. The web is pressed against the array of supports, thereby resulting in densified zones in the web at the locations geographically corresponding to the points of contact between the array of supports and the wet web.

The remainder of the web not compressed during this operation is referred to as the high bulk field. This high bulk field can be further dedensified by application of fluid pressure, such as with a vacuum type device or a blow-through dryer, or by mechanically pressing the web against the array of supports.

The web is dewatered, and optionally predried, in such a manner so as to substantially avoid compression of the high bulk field. This is preferably accomplished by fluid pressure, such as with a vacuum type device or blow-through dryer, or alternately by mechanically pressing the web against an array of supports wherein the high bulk field is not compressed. The operations of dewatering, optional predrying and formation of the densified zones can be integrated or partially integrated to reduce the total number of processing steps performed.

Subsequent to formation of the densified zones, dewatering, and optional predrying, the web is dried to completion, preferably still avoiding mechanical pressing. Preferably, from about 8% to about 55% of the tissue paper surface comprises densified knuckles having a relative density of at least 125% of the density of the high bulk field.

The array of supports is preferably an imprinting carrier fabric having a patterned displacement of knuckles that operate as the array of supports that facilitate the formation of the densified zones upon application of pressure. The pattern of knuckles constitutes the array of supports previously referred to.

Suitable imprinting carrier fabrics are disclosed in U.S. Pat. No. 3,301,746, issued to Sanford et al. on Jan. 31, 1967; U.S. Pat. No. 3,473,576, issued to Amneus on Oct. 21, 1969; U.S. Pat. No. 3,573,164, issued to Friedberg et al. on Mar. 30, 1971; U.S. Pat. No. 3,821,068, issued to Salvucci et al. on May 21, 1974; U.S. Pat. No. 3,974,025, issued to Ayers on Aug. 10, 1976; U.S. Pat. No. 4,239,065, issued to Trokhan on Dec. 16, 1980; U.S. Pat. No. 4,528,239, issued to Trokhan on Jul. 9, 1985; U.S. Pat. No. 5,098,522, issued to Smurkoski on Mar. 24, 1992; U.S. Pat. No. 5,275,700, issued to Trokhan on Jan. 4, 1994; U.S. Pat. No. 5,328,565, issued to Rasch et al., on Jul. 12, 1994; U.S. Pat. No. 5,334,289, issued to Trokhan et al. on Aug. 2, 1994; U.S. Pat. No. 5,496,624, issued to Stelljes, Jr. et al., on Mar. 5, 1996; U.S. Pat. No. 5,500,277, issued to Trokhan et al., on Mar. 19, 1996, U.S. Pat. No. 5,628,876, issued to Ayers et al., on May 13, 1997; and U.S. Pat. No. 5,679,222, issued to Rasch et al. on Oct. 21, 1997, the disclosures of which are incorporated by reference.

Preferably, the furnish is first formed into a wet web on a foraminous forming carrier, such as a fourdrinier wire. The web is dewatered and transferred to an imprinting fabric. The furnish can alternately be initially deposited on a foraminous supporting carrier that also operates as an imprinting fabric. Once formed, the wet web is dewatered and, preferably, thermally predried to a selected fiber consistency from about 40% to about 80%.

Dewatering is preferably performed with suction boxes or other vacuum devices or with blow-through dryers. The knuckle imprint of the imprinting fabric is impressed in the web as discussed above, prior to drying the web to completion. One method for accomplishing this is through application of mechanical pressure. This can be done, for example, by pressing a nip roll that supports the imprinting fabric against the face of a drying drum, such as a Yankee dryer, wherein the web is disposed between the nip roll and drying drum.

Also, preferably, the web is molded against the imprinting fabric prior to completion of drying by application of fluid pressure with a vacuum device such as a suction box, or with a blow-through dryer. Fluid pressure can be applied to induce impression of densified zones during initial dewatering, in a separate, subsequent process stage, or a combination thereof.

Uncompacted, nonpattern-densified tissue paper structures are described in U.S. Pat. No. 3,812,000, issued to Salvucci et al. on May 21, 1974 and U.S. Pat. No. 4,208,459, issued to Becker et al. on Jun. 17, 1980, both of which are incorporated by reference. In general, uncompacted, nonpattern-densified tissue paper structures are prepared by depositing a papermaking furnish on a foraminous forming wire such as a fourdrinier wire to form a wet web, draining the web and removing additional water without mechanical compression until the web has a fiber consistency of at least about 80%, and creping the web.

Water is removed from the web by vacuum dewatering and thermal drying. The resulting structure is a soft but weak, high bulk sheet of relatively uncompacted fibers. Bonding material is preferably applied to portions of the web prior to creping.

Compacted non-pattern-densified tissue structures are commonly known in the art as conventional tissue structures. In general, compacted, non-pattern densified tissue paper structures are prepared by depositing a papermaking furnish on a foraminous wire such as a fourdrinier wire to form a wet web, draining the web and removing additional water with the aid of a uniform mechanical compaction (pressing) until the web has a consistency of about 25%–50%, transferring the web to a thermal dryer such as a Yankee, and creping the web. Overall, water is removed from the web by vacuum, mechanical pressing and thermal means. The resulting structure is strong and generally of singular density, but very low in bulk, absorbency and softness.

Other suitable tissue paper structures and methods of making tissue paper structures useful with the present invention are disclosed in U.S. Pat. Nos. 3,994,771, issued to Morgan, Jr. et al. on Nov. 30, 1976; U.S. Pat. No. 4,225,382, issued to Kearney et al on Sep. 30, 1980; U.S. Pat. No. 4,300,981, issued to Carstens et al. on Nov. 17, 1981; U.S. Pat. No. 5,245,025, issued to Trokhan et al. on Sep. 14, 1993; U.S. Pat. No. 5,277,761, issued to Phan et al. on Jan. 11, 1994; U.S. Pat. No. 5,443,691, issued to Phan et al. on Aug. 22, 1995; U.S. Pat. No. 5,503,715, issued to Trokhan et al. on Apr. 2, 1996; U.S. Pat. No. 5,527,428, issued to Trokhan et al. on Jun. 18, 1996; U.S. Pat. No. 5,534,326, issued to Trokhan et al. on Jul. 9, 1996; U.S. Pat. No. 5,614,061, issued to Phan et al. on Mar. 25, 1997; U.S. Pat. No. 5,654,076, issued to Trokhan et al. on Aug. 5, 1997; U.S. Pat. No. 5,804,036, issued to Phan et al. on Sep. 8, 1998; U.S. Pat. No. 5,804,281, issued to Phan et al. on Sep. 8, 1998; U.S. Pat. No. 5,814,188 issued to Vinson et al. on Sep. 29, 1998; and U.S. Pat. No. 5,820,730, issued to Phan et al. on Oct. 13, 1998, the disclosures of which are incorporated herein by reference.

The tissue may also be made according to U.S. Pat. No. 5,411,636 issued to Hermans et al. on May 2, 1995 and EP 677612 published in the name of Wendt et al. on Oct. 18, 1995.

The tissue may be foreshortened, as is known in the art. Foreshortening can be accomplished by creping the paper from a rigid surface, and preferably from a cylinder. A Yankee drying drum is commonly used for this purpose. Creping is accomplished with a doctor blade as is well known in the art. Creping may be accomplished according to commonly assigned U.S. Patents: U.S. Pat. No. 6,048,938 issued to Neal et al. on Apr. 11, 2000; U.S. Pat. No. 5,942,085 issued to Neal et al. on Aug. 24, 1999; U.S. Pat. No. 5,865,950 issued to Vinson et al. on Feb. 2, 1999; U.S. Pat. No. 4,191,756 issued to Sawdai on May 4, 1980; or U.S. Ser. No. 09/042,936 filed Mar. 17, 1998, the disclosures of which patents are incorporated herein by reference.

Alternatively or additionally, foreshortening may be accomplished via wet microcontraction as taught in commonly assigned U.S. Pat. No. 4,440,597, issued Apr. 3, 1984 to Wells et al., the disclosure of which is incorporated herein by reference.

The papermaking fibers utilized for the present invention will normally include fibers derived from wood pulp. Other cellulosic fibrous pulp fibers, such as cotton, bagasse, jute, etc., can be utilized and are intended to be within the scope of this invention. Synthetic fibers, such as rayon, nylon, polyester, polyethylene, polypropylene fibers, and MICROBAN®, a material manufactured by Microban Products Co. of Huntersville, N.C., can also be utilized in combination with natural cellulosic fibers. One exemplary polyethylene fiber that can be utilized is PULPEX®, available from Hercules, Inc. of Wilmington, Del.

Applicable wood pulps include chemical pulps, such as kraft, sulfite, solvent, and soda pulps, as well as mechanical pulps including, for example, groundwood, thermomechanical pulp and chemically modified thermomechanical pulp. Chemical pulps, however, are preferred since they impart a superior tactile sense of softness to tissue sheets made therefrom. Pulps derived from both deciduous trees (hereafter, also referred to as "hardwood") and coniferous trees (hereafter, also referred to as "softwood") can be utilized. Also useful in the present invention are fibers derived from recycled paper, which can contain any or all of the above categories as well as other non-fibrous materials such as fillers and adhesives used to facilitate the original papermaking.

In addition to papermaking fibers, the papermaking furnish used to make tissue paper structures can have other components or materials added thereto. The types of additives desirable will be dependent upon the particular end use of the tissue sheet contemplated.

For example, in the tissue products of the present invention high wet strength is a desirable attribute. Thus, it is desirable to add to the papermaking furnish chemical substances known in the art as "wet strength" resins.

Useful wet strength resins include those that are generally cationic in character. Examples of wet strength resins suitable for providing permanent wet strength generation, include cationic polyamide-epichlorohydrin resins such as those described in U.S. Pat. No. 3,700,623, issued to Keim on Oct. 24, 1972, and U.S. Pat. No. 3,772,076, issued to Keim, on Nov. 13, 1973, both of which are incorporated by reference.

A useful cationic polyamide-epichlorohydrin wet strength resin suitable for use with the present invention is KYMENE® 557H, commercially available from Hercules, Inc. of Wilmington, Del.

Other suitable wet strength resins include latex based wet strength agents and polyacrylamide resins such as those described in U.S. Pat. No. 3,556,932, issued to Coscia et al. on Jan. 19, 1971, and U.S. Pat. No. 3,556,933, issued to Williams et al. on Jan. 19, 1971, both of which are incorporated herein by reference. One commercial source of polyacrylamide resin is American Cyanamid Co. of Stamford, Conn., which markets one such resin under the name of PAREZ® 631 NC.

Other water-soluble cationic resins which may be used in this invention include urea formaldehyde and melamine formaldehyde resins. The more common functional groups of these polyfunctional resins are nitrogen containing groups such as amino groups and methylol groups attached to nitrogen. Polyethylenimine type resins may also be used in the present invention.

The permanent wet strength resin is applied in an amount of from about 0.05% to 10% by weight of the tissue paper, preferably from about 0.1% to 5% by weight of the tissue paper, more preferably from about 0.2% to 2%, and most preferably from about 0.3% to 1% by weight of the tissue paper.

Japanese Industrial Standard JIS P4501 (1993), incorporated herein by reference, describes an "Easiness to Loosen in Water" test. This test is a measurement of the water disintegrability of the tissue sheet. It is desirable that the tissue products of the present invention have an "Easiness to Loosen in Water" test value of greater than about 100 seconds.

The "Easiness to Loosen in Water" test procedure as disclosed in JIS P4501 is as follows: A beaker is filled with 300 ml of water (having a temperature of 20±5° C.). The beaker is placed on a magnetic stirrer, the rotor of which is adjusted so as to have a rotation speed of 600±10 rounds/minute. A disc like rotor 35 mm in diameter and 12 mm in thickness is used for this purpose. A square sample (i.e.; one side measuring 114±2 mm) of a single ply of the tissue sheet to be tested is placed in the beaker. A timer is then started. The rotation speed of the rotor is reduced to approximately 500 rounds/minute and then goes back up according to the loosening of the tissue sample. When the rotor speed goes back up to 540 rounds/minute, the timer is stopped and the time measured to a unit of a second is recorded. Five samples of the the tissue sheet are tested and an average based on the five tests is determined. In order to meet the "Easiness to Loosen in Water" standard under JIS P4501 the tissue sheet must exhibit a time of 100 seconds or less.

Other chemical additives which may optionally be added to the pulp furnish of the present invention include but are not limited to additives such as: temporary wet strength agents, dry strength agents, fillers, lint control agents, sizing agents and softening agents.

Suitable softening agents for use in the present invention include those disclosed in commonly assigned U.S. Pat. Nos. 5,059,282 issued to Ampulski et al. on Oct. 22, 1991; U.S. Pat. No. 5,215,626 issued to Ampulski et al. on Jun. 1, 1993; U.S. Pat. No. 5,246,545 issued to Ampulski et al. on Sep. 21, 1993; U.S. Pat. No. 5,264,082 issued to Phan et al. on Nov. 23, 1993; U.S. Pat. No. 5,415,737 issued to Phan et al. on May 16, 1995; U.S. Pat. No. 5,510,000 issued to Phan et al. on Apr. 23, 1996; U.S. Pat. No. 5,525,345 issued to Warner et al. on Jun. 11, 1996; U.S. Pat. No. 5,538,595 issued to Trokhan et al. on Jul. 23, 1996; U.S. Pat. No. 5,543,067 issued to Phan et al. on Aug. 6, 1996; U.S. Pat. No. 5,814,188 issued to Vinson et al. on Sep. 29, 1998, the disclosures of which are incorporated herein by reference.

B. Antiviral Composition

The antiviral composition of the present invention comprises one or more antiviral agents.

1. Pyrrolidone Carboxylic Acid

The antiviral agent of the present invention most preferably comprises pyrrolidone carboxylic acid. While not wishing to be bound by theory, it is believed that the unique properties of pyrrolidone carboxylic acid in combination with the tissue web render the tissue product of the present invention highly efficacious against common influenza and cold viruses such as Rhinoviruses.

Furthermore, transfer of the antiviral composition from the tissue to the skin can potentially protect those skin regions which come in contact with the virus. Yet further, because these antiviral compositions tend to be mild, the potential for skin irritation and stinging in these areas is greatly reduced.

Even further, it is believed that the unique structure of pyrrolidone carboxylic acid in combination with the tissue web renders the tissue product highly efficacious against Rhinovirus (especially Rhinovirus-14) over prolonged exposure periods. Thus, potential transfer of pyrrolidone carboxylic acid to the skin may result in viral kill in the tissue and on the skin surface for a prolonged exposure period. Hence, overall efficacy of the virucidal product is enhanced.

Unlike other antiviral tissue products, it is also believed that the unique moisturization potential of the antiviral agent of the present invention may improve skin health and reduce the possibility of skin irritation versus other virucidal tissue products.

Pyrrolidone carboxylic acid, which is also referred to as pyroglutamic acid has two stereoisomers (D and L). Both stereoisomers are suitable for use in the present invention. Each or mixtures thereof are preferred for use herein. Furthermore, blends of the two stereoisomers may also be used. The L stereoisomer is most preferred.

The D stereoisomer of pyroglutamic acid is also known by the following names: D-Proline, 5-oxo-(+)-2-Pyrrolidone-5-carboxylic acid, (+)-Pyroglutamic acid, (R)-2-Pyrrolidone-5-carboxylic acid, 5-Oxo-D-proline, D-2-Pyrrolidone-5-carboxylic acid, D-Pyroglutamic acid, D-Pyrrolidinonecarboxylic acid, and D-Pyrrolidonecarboxylic acid.

The L stereoisomer of pyroglutamic acid is also known by the following names: L-Proline, 5-oxo-(-)-2-Pyrrolidone-5-carboxylic acid, (-)-Pyroglutamic acid, (5S)-2-Oxopyrrolidine-5-carboxylic acid, (S)-(-)-2-Pyrrolidone-5-carboxylic acid, (S)-2-Pyrrolidone-5-carboxylic acid, (S)-5-Oxo-2-pyrrolidinecarboxylic acid, (S)-Pyroglutamic acid, 2-L-Pyrrolidone-5-carboxylic acid, 2-Pyrrolidinone-5-carboxylic acid, 5-Carboxy-2-pyrrolidinone, 5-Oxo-L-proline, 5-Oxoproline, 5-Pyrrolidinone-2-carboxylic acid, Glutimic acid, Glutiminic acid, L-2-Pyrrolidone-5-carboxylic acid, L-5-Carboxy-2-pyrrol id inone, L-5-Oxo-2-pyrrolidinecarboxylic acid, L-5-Oxoproline, L-Glutamic acid, .gamma.-lactam, L-Glutimic acid, L-Glutiminic acid, L-Pyroglutamic acid, L-Pyrrolidinonecarboxylic acid, L-Pyrrolidonecarboxylic acid, Oxoproline, PCA, Pidolic acid, Pyroglutamic acid, Pyrrolidinonecarboxylic acid, Pyrrolidone-5-carboxylic acid, and Pyrrolidonecarboxylic acid.

The DL form of pyroglutamic acid (a mixture of the D and L stereoisomers) is known by the following names:

DL-Proline, 5-oxo-(.+−.)-2-Pyrrolidone-5-carboxylic acid, (.+−.)-Pyroglutamic acid, 5-Oxo-DL-proline, DL-2-Pyrrolidinone-5-carboxylic acid, DL-2-Pyrrolidone-5-carboxylic acid, DL-Pyroglutamate, DL-Pyroglutamic acid, DL-Pyrrolidonecarboxylic acid, and Oxoproline. The DL form is also commercially available under the tradename Ajidew® A 100.

Some of the above-listed stereoisomers are commercially available from UCIB, France via Barnet Products Corp. of Englewood Cliffs, N.J. under the trade name of Pidolidone® and from Ajinomoto Corp., Japan under the trade name of Ajidew® A-100. Metal salts of pyrrolidone carboxylic acid are also commercially available and can produce pyrrolidone carboxylic acid by acidification of the salt solution with mineral or other organic acids.

The most common is sodium pyrrolidone carboxylate from UCIB, France via Barnet Products Corp. of Englewood Cliffs, N.J. under the trade name of Nalidone® and from Ajinomoto Corp., Japan under the trade names of Ajidew® N-50 and Ajidew® NL-50. Other such salts of pyrrolidone carboxylic acid include but are not limited to copper, iron, potassium, aluminum, manganese, and zinc. Other compounds of pyrrolidone carboxylic acid that may be used include arginine PCA, betaine PCA, and lysine PCA.

Pyrrolidone carboxylic acid comprises from about 0.05% to 100% of the antiviral composition by weight, preferably from about 0.5% to 80% of the antiviral composition by weight, and most preferably from about 5% to 70% by weight.

2. Other Optional Antiviral Agents

In addition to pyrrolidone carboxylic acid, other antiviral agents may also be optionally used in the present invention.

a. Optional Organic Acids

In addition to pyrrolidone carboxylic acid, other organic acids may be optionally added to the antiviral composition. These include but are not limited to organic acids such as ascorbic acid and other carboxylic acids.

Suitable other carboxylic acids include but are not limited to alpha hydroxy acids such as $C_1$ to $C_{12}$ saturated, unsaturated, or mixtures thereof of carboxylic acids possessing 1 to 4 carboxylic acid groups and having at least one hydroxyl group substituted on the $C_2$ alpha carbon with additional hydroxyl and other functionalities (i.e.; phenyl, amino, alkyl, etc.) optionally bound along the carbon chain and aromatic ring(s). A non-inclusive list of alpha hydroxy acids which may be used includes: 2-hydroxyhexanoic acid, 2-hydroxyoctanoic acid, 2-hydroxydecanoic acid, 2-hydroxydodecanoic acid, 2-hydroxycaprylic acid, citric acid, tartaric acid, mandelic acid, malic acid, glycolic acid, lactic acid, gluconic acid, hydroxycaprylic acid, 2-hydroxypropionic acid, 2-hydroxybutanoic acid, 2-hydroxypentanoic acid, and mixtures thereof.

Other examples of carboxylic acids useful with this invention include beta hydroxy acids such as $C_1$ to $C_{12}$ saturated, unsaturated, aromatic, or mixtures thereof of carboxylic acids possessing 1 to 4 carboxylic acid groups and having at least one hydroxyl group substituted on the $C_3$ beta carbon with additional hydroxyl and other functionalities (i.e.; phenyl, amino, hydroxyl, alkyl, etc.) optionally bound along the carbon chain or aromatic ring(s). A non-inclusive list of beta hydroxy acids useful with this invention includes: 3-hydroxyhexanoic acid, 3-hydroxyoctanoic acid, 3-hydroxydecanoic acid, 3-hydroxydodecanoic acid, 3-hydroxycaprylic acid, salicylic acid, 5-octanoyl salicylic acid, 3-hydroxybutanoic acid, 3-hydroxypentanoic acid, 3-hydroxypropionic acid, and mixtures thereof.

A non-inclusive list of other carboxylic acids useful with this invention includes $C_1$ to $C_{12}$ saturated, unsaturated, aromatic, or mixtures thereof of carboxylic acids possessing 1 to 4 carboxylic acid groups with optional functional groups (i.e.; phenyl, amino, alkyl, etc.) substituted along the carbon chain or on the aromatic ring(s) such as propionic acid, hexanoic acid, octanoic acid, decanoic acid; $C_1$ to $C_{12}$ carboxylic acids possessing 1 to 4 carboxylic acid groups wherein a hydroxyl group(s) is substituted on carbon number(s) $C_4$ or above such as 4-hydroxyhexanoic acid, 5,6-dihydroxyhexanoic acid, 6-hydroxyhexanoic acid, 4-hydroxyoctanoic acid, 5-hydroxyoctanoic acid, 6-hydroxyoctanoic acid, 6,7,8-trihydroxyoctanoic acid, 8-hydroxyoctanoic acid, 4-hydroxydecanoic acid, 5-hydroxydecanoic acid, 6-hydroxydecanoic acid, 7-hydroxydecanoic acid, 8-hydroxydecanoic acid, 9-hydroxydecanoic acid, 10-hydroxydecanoic acid, 4-hydroxydodecanoic acid, 5-hydroxydodecanoic acid, 6-hydroxydodecanoic acid, 11-hydroxydodecanoic acid, and 12-hydroxydodecanoic acid; benzoic acid; phthalic acid; acetylsalicylic acid; dehydroacetic acid; sorbic acid; succinic acid; glutaric acid; adipic acid; sebacic acid; maleic acid; folic acid; acetic acid; ethylenediaminetetraacetic acid; glycolic acid; and mixtures thereof.

The optional organic acid comprises from about 0.1% to 80% of the antiviral composition by weight, preferably from about 2% to 50%, of the antiviral composition by weight, and more preferably from about 5% to 20% of the antiviral composition by weight.

b. Optional Metal Salts

Metal salts may also be used as an optional component of the antiviral agent of the present invention. Suitable metal salts include those disclosed in U.S. Ser. No. 09/421,131 filed Oct. 19, 1999; Ser. No. 09/421,179 filed Oct. 19, 1999; and Ser. No. 09/458,750 filed Dec. 10, 1999, the disclosures of which are incorporated herein by reference.

Suitable metal salts include, but are not limited to, salts of metals selected from the groups consisting of Groups I(A, B), II(A, B), IIIA, IV(A, B), VIB, VIII, rare earth compounds, and combinations thereof. More preferably, metal salts include salts of metals selected from the group consisting of Mn, Ag, Zn, Sn, Fe, Cu, Al, Ni, Co, Ti, Zr, Cr, La, Bi, K, Cd, Yb, Dy, Nd, Ce, Tl, Pr, and combinations thereof. Even more preferably, metal salts include salts of metals selected from the group consisting of Mn, Ag, Zn, Sn, Fe, Cu, Al, Ni, Co, Ti, Zr, Cr, La, and combinations thereof. Most preferably, the metal salts include salts of metals selected from the group consisting of Cu, Fe, and combinations thereof.

More particularly, the metal salts include, but are not limited to, dermatologically acceptable metal chelates and salts like bishistidine complexes, bromides, chondroitin sulfate, chromites, cyanides, dipicolinates, ethylhexanoates, glycerolate complex, methoxides, polyphosphonates, paraphenolsulfonates, perchlorates, phenolsulfonates, selenides, stearates, thiocyanates, tripolyphosphates, tungstates, phosphates, carbonates, para-aminobenzoate, paradimethylaminobenzoates, hydroxides, para-methoxycinnamate, naphthenates, stearates, caprates, laurates, myristates, palmitates, oleates, picolinates, pyrithiones, fluorides, aspartates, gluconates, iodides, oxides, nitrites, nitrates, phosphates, pyrophosphates, sulfides, mercaptopyridine-oxides (e.g., zinc pyrithione), nicotinates, and nicotinamides, hinokitiol, acetates, ascorbates, chlorides, benzoates, citrates, fumarates, gluconates, glutarates, lactates, malates, malonates, salicylates, succinates, sulfates, undecylates, and combinations thereof.

More preferably, the metal salts are selected from the group consisting of phosphates, carbonates, para-aminobenzoate, paradimethylaminobenzoates, hydroxides, para-methoxycinnamate, naphthenates, stearates, caprates, laurates, myristates, palmitates, oleates, picolinates, pyrithiones, fluorides, aspartates, gluconates, iodides, oxides, nitrites, nitrates, phosphates, pyrophosphates, sulfides, mercaptopyridine-oxides (e.g., zinc pyrithione), nicotinates, and nicotinamides, hinokitiol, acetates, ascorbates, chlorides, benzoates, citrates, fumarates, gluconates, glutarates, lactates, malates, malonates, salicylates, succinates, sulfates, undecylates and combinations thereof.

Even more preferably, the metal salts are selected from the group consisting of fluorides, aspartates, gluconates, iodides, oxides, nitrites, nitrates, phosphates, pyrophosphates, sulfides, mercaptopyridine-oxides (e.g., zinc pyrithione), nicotinates, and nicotinamides, hinokitiol, acetates, ascorbates, chlorides, benzoates, citrates, fumarates, gluconates, glutarates, lactates, malates, malonates, salicylates, succinates, sulfates, undecylates, and combinations thereof.

Even more preferably, the metal salts and complexes are: acetates, ascorbates, chlorides, benzoates, citrates, fumarates, gluconates, glutarates, lactates, malates, malonates, salicylates, succinates, sulfates, undecylates, and combinations thereof.

Most preferably, the metal salts are selected from the group consisting of copper pidolate, L-FER pidolate, cuprous sulfate, cupric sulfate, ferrous chloride, ferric chloride, cuprous chloride, cupric chloride, ferrous sulfate, ferric sulfate, and combinations thereof.

Without being limited by theory, it is believed that in the compositions of the present invention, the pyroglutamic acid and metal salt complex to form a metal-acid complex which has been found to provide a synergistic immediate and residual anti-viral efficacy.

In the compositions of the present invention, the optional metal salt is present in amount such that the final metal ion preferably comprises from about 0.001% to about 20%, by weight of the composition, more preferably, from about 0.01% to about 10%, and even more preferably from about 0.05% to about 5%.

Alternatively, the pyroglutamic acid and metal salt may be complexed prior to making the compositions of the present invention thereby forming a pyroglutamic acid-metal complex. In this instance, the complex is present in an amount of from about 0.001% to about 20%, by weight of the composition, and preferably from about 0.01% to about 10%. A preferred metal salt is copper sulfate.

3. Surfactant(s)

The antiviral composition of the present invention may also include an optional surfactant.

While not wishing to be limited by theory, it is believed that the optional surfactant can aid in solubilizing the lipid shell layer of the enveloped class of viruses. This solubilization of the lipid shell enhances the ability of the antiviral acids to penetrate into the virus structure and deactivate it.

Suitable surfactants include but are not limited to nonionic, cationic, anionic, amphoteric, and zwitterionic surfactants.

Examples of suitable nonionic surfactants include but are not limited to alkoxylated alcohols having an HLB of about 8 to 20 and the following formula:

wherein $R=C_2-C_{50}$ and may be either branched, unsaturated, or saturated $n=10-40$ X=hydrogen, methyl, or ethyl A suitable alkoxylated alcohol is polyoxypropylene (5) polyoxyethylene (20) cetyl ether commercially available as PROCETYL AWS manufactured by Croda Incorporated of Parsippany, N.J.

A preferred alkoxylated alcohol is a $C_{12}$ to $C_{15}$ polyethoxylated alcohol commercially available as Tomadol 25-12 from Tomah Products Incorporated of Reserve, Louisiana or as Neodol 25-12 from Shell Chemicals of Houston, Tex. (condensation product of $C_{12}-C_{15}$ linear alcohols with an average of about 12 moles of ethylene oxide).

Other suitable ethoxylated alcohols include TERGITOL 15-S-9 (the condensation product of $C_{11}-C_{15}$ linear alcohols with an average of about 9 moles of ethylene oxide), marketed by Union Carbide Corporation of Danbury, Conn.; and NEODOL 23-6.5T (condensation product of $C_{12}-C_{13}$ linear alcohols with an average of about 6.5 moles of ethylene oxide that has been distilled (topped) to remove certain impurities), and the PLURAFAC brand name surfactants marketed by BASF Corp. of Mount Olive, N.J., such as PLURAFAC A-38 (a condensation product of a $C_{18}$ straight chain alcohol with an average of about 27 moles of ethylene oxide).

Other examples of ethoxylated alcohol surfactants are supplied by Imperial Chemical Company (ICI) of Wilmington, Del. These include the class of BRIJ surfactants and mixtures thereof, such as BRIJ 76 (i.e., Steareth-10) and BRIJ 56 (i.e., Ceteth-10).

Other suitable nonionic surfactants for use in the present invention include alkylglycosides; alkylglycoside ethers as described in U.S. Pat. No. 4,011,389, issued to Langdon et al. on Mar. 8, 1977; alkylpolyethoxylated esters such as PEGOSPERSE 1000 MS, available from Lonza Inc. of Fair Lawn, N.J.; ethoxylated sorbitan mono-, di- and/or tri-esters of $C_{12}-C_{18}$ fatty acids having an average degree of ethoxylation of from about 2 to about 20, preferably from about 2 to about 10, such as TWEEN 60 (sorbitan esters of stearic acid having an average degree of ethoxylation of about 20), TWEEN 20 (sorbitan esters of lauric acid having an average degree of ethoxylation of about 20) and TWEEN 61 (sorbitan esters of stearic acid having an average degree of ethoxylation of about 4).

Another type of suitable surfactant for use in the present invention includes AEROSOL OT, a dioctyl ester of sodium sulfosuccinic acid marketed by Cytec Industries Inc. of West Paterson, N.J.

Still other types of suitable surfactants for use in the present invention, include silicone copolymers such as those made by General Electric of Fairfield, Conn. Suitable silicone copolymers include General Electric's SF 1188 (a copolymer of a polydimethylsiloxane and a polyoxyalkylene ether) and General Electric's SF 1228 (a silicone polyether copolymer).

The optional surfactant comprises from about 0.01% to 10% of the antiviral composition by weight, preferably 0.1% to 5%, and most preferably from about 0.2% to 2%.

Other Optional Components of the Antiviral Tissue

Moisture Barrier:

The antiviral tissue may optionally include one or more moisture barriers. The optional moisture barrier may be joined, connected to, placed on, or impregnated into the fibrous ply. The antiviral composition may optionally be applied to the moisture barrier.

Preferred moisture barriers and a method for making moisture barriers suitable for use with the present invention are disclosed in commonly assigned U.S. Pat. No. 5,968,853 issued to Kelly et al. on Oct. 19, 1999, U.S. Ser. No. 09/120,828 filed Jul. 22, 1998, and U.S. Ser. No. 09/287,857 filed Apr. 7, 1999, the disclosures of which are incorporated herein by reference.

Suitable moisture barriers are also disclosed in Great Britain 1,599,875 published in the name of Sweens et al. on Oct. 7, 1981 and EP 0144658 published in the name of Endres on Jun. 9, 1985.

Moisture barriers are also disclosed in: U.S. Pat. No. 6,054,020 issued to Goulet et al. on Apr. 25, 2000; WO 97/41301 published in the name of McFarland et al. on Nov. 6, 1997; WO 00/00698 published in the name of Hsu et al. on Jan. 6, 2000; Canada 2,239,927 published in the name of McCullough on Jan. 1, 1999.

Suitable methods for joining fibrous plies with one another and/or with one or more moisture barriers include but are not limited to ply bonding such as disclosed in commonly assigned U.S. Pat. Nos. 3,414,459 issued to Wells on Dec. 3, 1968; U.S. Pat. No. 3,867,225 issued to Nystrand on Feb. 18, 1975; U.S. Pat. No. 4,481,243 issued to Allen on Nov. 6, 1984; and U.S. Pat. No. 5,294,475 issued to McNeil on Mar. 15, 1994; the disclosure of which are incorporated herein by reference.

Water Soluble Film Carrier:

The antiviral composition of the present invention may also optionally include a water soluble film carrier. A suitable water soluble film carrier for this purpose is disclosed in U.S. Ser. No. 09/342,777 filed on Jun. 29, 1999, the disclosure of which is incorporated herein by reference.

Lotion:

The tissue of the present invention may optionally include a lotion. The antiviral composition of the present invention may optionally be included as a component of the optional lotion. If the antiviral composition is included as a component of the lotion, the antiviral composition comprises from about 0.05% to 80% of the lotion by weight, preferably from 0.5% to 70% of the lotion by weight, and more preferably from 5% to 60% of the lotion by weight. If the antiviral composition is included as a component of the lotion, pyrrolidone carboxylic acid comprises from about 0.05% to 100% of the antiviral composition contained in the lotion by weight, preferably from about 0.5% to 80% of the antiviral composition contained in the lotion by weight, and most preferably from about 5% to 70% of the antiviral composition contained in the lotion by weight.

Lotions suitable for this purpose are disclosed in U.S. Pat. Nos. 4,112,167 issued to Dake et al. on Sep. 5, 1978; U.S. Pat. No. 4,481,243 issued to Allen on Nov. 6, 1984; U.S. Pat. No. 4,513,051 issued to Lavash on Apr. 23, 1985; U.S. Pat. No. 5,525,345 issued to Warner et al. on Jun. 11, 1996; U.S. Pat. No. 5,716,692 issued to Warner et al. on Feb. 10, 1998; U.S. Pat. No. 5,830,487 issued to Klofta et al. on Nov. 3, 1998; and U.S. Pat. No. 6,238,682 filed Mar. 12, 1998, the disclosures of which are incorporated herein by reference.

Preferred lotions suitable for this purpose are disclosed in U.S. Pat. Nos. 5,059,282 issued to Ampulski et al. on Oct. 22, 1991; U.S. Pat. No. 5,164,046 issued to Ampulski et al. on Nov. 17, 1992; U.S. Pat. No. 5,385,643 issued to Ampulski on Jan. 31, 1995; U.S. Pat. No. 5,389,204 issued to Ampulski on Feb. 14, 1995; U.S. Pat. No. 5,814,188 issued to Vinson et al. on Sep. 29, 1998; the disclosures of which are incorporated herein by reference.

Lotions preferred for use with the present invention include polysiloxane based lotions.

Types of polysiloxane materials which are suitable for use in the present invention include polymeric, oligomeric, copolymeric, and other multiple-monomeric siloxane materials. As used herein, the term polysiloxane and silicone are used interchangeably. They shall include all of such polymeric, oligomeric, copolymeric and other multiple-monomeric siloxane materials. Additionally, the polysiloxane can be either a straight chain, a branched chain or have a cyclic structure.

Preferred polysiloxane materials include those having monomeric siloxane units of the following structure:

wherein, $R_1$ and $R_2$ for each siloxane monomeric unit can independently be any alkyl, aryl, alkenyl, alkaryl, aralkyl, cycloalkyl, halogenated hydrocarbon, or other radical. Any of such radicals can be substituted or unsubstituted. $R_1$ and $R_2$ radicals of any particular monomeric unit may differ from the corresponding functionalities of the next adjoining monomeric unit.

Additionally, the radicals can be either a straight chain, a branched chain, or have a cyclic structure. The radicals $R_1$ and $R_2$ can, additionally and independently, be other silicone functionalities such as, but not limited to siloxanes, polysiloxanes, and polysilanes. The radicals $R_1$ and $R_2$ can also contain any of a variety of organic functionalities including, for example, alcohol, carboxylic acid, and amine functionalities.

Preferred polysiloxanes include straight chain organopolysiloxane materials of the following general formula:

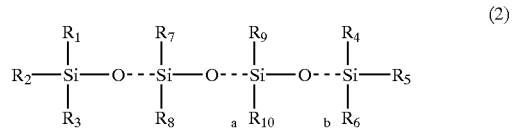

wherein each $R_1$–$R_9$ radical can independently be any $C_1$–$C_{10}$ unsubstituted alkyl or aryl radical, and $R_{10}$ is any substituted $C_1$–$C_{10}$ alkyl or aryl radical. Preferably each $R_1$–$R_9$ radical is independently any $C_1$–$C_4$ unsubstituted alkyl group. Those skilled in the art will recognize that technically there is no difference whether, for example, $R_9$ or $R_{10}$ is the substituted radical. Preferably the mole ratio of b to (a+b) is between 0 and about 20%, more preferably between 0 and about 10%, and most preferably between about 1% and about 5%.

In one particularly preferred embodiment, $R_1$–$R_9$ are methyl groups and $R_{10}$ is a substituted or unsubstituted alkyl, aryl, or alkenyl group. Such material shall be generally described herein as polydimethylsiloxane which has a particular functionality as may be appropriate in that particular case. Exemplary polydimethylsiloxanes include, for example, polydimethylsiloxane, polydimethylsiloxane having an alkyl hydrocarbon $R_{10}$ radical and polydimethylsiloxane having one or more amino, carboxyl, hydroxyl, ether, polyether, aldehyde, ketone, amide, ester, thiol and/or other $R_{10}$ functionalities including alkyl and alkenyl analogues of such functionalities. For example, an amino functional alkyl group as $R_{10}$ could be an amino-functional or an aminoalkylfunctional polydimethylsiloxane. The exemplary listing of these functional-polydimethylsiloxanes is not meant to thereby exclude others not specifically listed.

A preferred polydimethylsiloxane is CM 849 available from General Electric of Fairfield, Conn.

Viscosity of polysiloxanes useful for this invention may vary as widely as the viscosity of polysiloxanes in general vary, so long as the polysiloxane is flowable or can be made to be flowable for application to the tissue paper. This includes, but is not limited to, viscosity as low as about 25 centistokes to about 20,000,000 centistokes or even higher. High viscosity polysiloxanes which themselves are resistant to flowing can be effectively deposited upon the tissue paper webs by such methods as, for example, emulsifying the polysiloxane in surfactant or providing the polysiloxane in solution with the aid of a solvent, such as hexane, listed for exemplary purposes only. Particular methods for applying polysiloxanes to tissue paper webs are discussed in more detail below.

The optional lotion can be applied to the tissue paper web after the web has been dried, i.e. a "dry web" addition method. The lotion is applied in an amount of from about 0.01% to about 40% by weight of the tissue paper web. Preferably, the lotion is applied in an amount of from about 0.1% to about 25% by weight of the tissue paper web, most preferably from about 0.5% to about 18% by weight of the web.

The lotion can also be applied non-uniformly to the surface(s) of the tissue paper web. By "non-uniform" is meant that the amount, pattern of distribution, etc. of the lotion can vary over the surface of the paper. For example, some portions of the surface of the tissue paper web can have greater or lesser amounts of lotion, including portions of the surface that do not have any lotion on it.

An example of non-uniform application is where the tissue structure contains differing amounts and differing compositions of various formulations throughout its structure or alternatively where some zones may contain no lotion at all as taught by commonly assigned U.S. Pat. No. 4,481,423 issued to Allen on Nov. 6, 1984 and U.S. Pat. No. 5,814,188 issued to Vinson et al. on Sep. 29, 1998 the disclosures of which are incorporated herein by reference.

For instance in a two ply tissue structure, a lotion containing an antiviral composition might be applied to the two outer surfaces of the paper structure while an antiviral composition is applied to the two inner surfaces of the paper structure. Or in a three ply paper structure, the inside ply might contain the lotion while the user side of the two outside plies contains a skin lotion having an antiviral composition.

Additional examples include adding a lotion not containing any antiviral composition to the outside plies. The lotion might be an ingredient such as dimethicone which would transfer to the skin upon wiping to form a protective layer on the skin. Or, this lotion might transfer another active to the skin such as a sunblock, or skin healing additive.

While this lotion would be applied to the outside plies, the antiviral composition could be applied on the inside of one or both outside plies to produce the antiviral killing activity within the tissue. With the antiviral composition on the inside of the tissue, and the lotion applied to the outside, the antiviral killing activity would most probably be confined to the inside of the tissue rather than the user's skin surface. There are numerous permutations of these approaches.

The lotion can be applied to the tissue paper web at any point after it has been formed. Preferably the lotion is applied after the tissue web has been dried. For example, the lotion can be applied to the tissue paper web after it has been creped from a Yankee dryer, but prior to calendering, i.e., before being passed through calendar rolls. The lotion can also be applied to the paper web after it has passed through such calendar rolls and prior to being wound up on a parent roll. Usually, it is preferred to apply the lotion to the tissue paper as it is being unwound from a parent roll and prior to being wound up on smaller, finished paper product rolls.

The lotions of the present invention may be applied to the tissue paper by spraying the composition onto the tissue paper web or by gravure coating and extrusion coating methods. Gravure coating and extrusion coating methods are preferred such as those taught by U.S. Pat. No. 5,246,546, issued to Ampulski on Sep. 21, 1996 and incorporated herein by reference.

Treating Tissue Paper With Compositions of the Present Invention

In preparing virucidal tissue products according to the present invention, the antiviral composition and the optional lotion (whether the optional lotion includes or does not include an antiviral composition) may be applied to at least one surface of a tissue paper web. They may be applied uniformly or discretely to the tissue paper web. A non-limiting example of discrete addition to the tissue paper web is disclosed in U.S. Pat. No. 5,814,188 issued to Vinson et al. on Sep. 29, 1998, the disclosure of which is incorporated herein by reference.

The antiviral composition and the optional lotion may be applied in a continuous pattern or discontinuous pattern. Suitable application methods include those disclosed in U.S. Pat. Nos. 4,481,243 issued to Allen on Nov. 6, 1984; U.S. Pat. No. 5,720,966 issued to Ostendorf on Feb. 24, 1998; and U.S. Pat. No. 5,814,188 issued to Vinson et al. on Sep. 29, 1998, the disclosures of which are incorporated herein by reference.

Suitable methods include spraying, dipping, soaking, printing (e.g., flexographic printing), coating (e.g., gravure coating), extrusion, or combinations of these application techniques, e.g. spraying the composition on a rotating surface, such as a calendar roll, that then transfers the composition to the surface of the paper web. The composition can be applied either to one surface of the tissue paper web, or both surfaces.

The compositions of this invention can also be applied non-uniformly to the surface(s) of the tissue paper web. By "non-uniform" is meant that the amount, pattern of distribution, etc. of the antiviral agent can vary over the surface of the paper. For example, some portions of the surface of the tissue paper web can have greater or lesser amounts of the composition, including portions of the surface that do not have any composition on it.

An example of non-uniform application is where the tissue structure contains differing amounts and differing compositions of various formulations throughout its structure or alternatively where some zones may contain no lotion at all as taught by U.S. Pat. No. 4,481,243 issued to Allen on Nov. 6, 1984 and incorporated herein by reference.

The amount of antiviral composition or lotion containing an antiviral composition that is applied to the tissue is based upon the amount of pyrrolidone carboxylic acid which is added to the tissue on a dry weight basis. The amount of pyrrolidone carboxylic acid applied to the tissue is from about 0.05% to 50% by weight, preferably about 0.1% to 25% by weight, and more preferably from about 0.2% to 15% by weight. The amount of antiviral composition on the paper must be optimized in order to achieve effective inactivation of the virus. The pH of the antiviral tissue paper is about 6 or less, preferably less than about 4.5, and most preferably less than about 3.

Virucidal Assay Procedure

PROTOCOL SUMMARY

A suspension of high titre Rhinovirus type 14 (hereinafter referred to as "RV-14") is inoculated on a disc of tissue paper which has been previously placed in a Buchner funnel filtration device. The tissue is exposed to the virus for one minute. Immediately following the 1 minute exposure period, the virus aliquot is collected from the tissue by dispensing elution media onto the surface of the tissue and immediately applying vacuum suction. The virus aliquot is collected in a sterilized test tube, titered by 10-fold serial dilution, and assayed for the presence of virus.

The appropriate virus controls, cytotoxicity controls, and neutralization controls are assayed in parallel. Antiviral properties of the tissue product are evaluated and compared to untreated tissues and a reduction in virus titer determined.

CULTURE MATERIALS

Stock Virus

Rhinovirus type 14 strain 1059 is obtained from the American Type Culture Collection (ATCC), Rockville, Md. (catalogue No. VR-284).

The stock virus is prepared by collecting the supernatant culture fluid from 75%–100% infected culture cells. The cells are disrupted and cell debris removed by centrifugation. The supernatant is removed and may be stored at $\leq -70$ degrees centigrade until use. The supernatant is thawed (if frozen) and centrifuged at 100,000 RPM for 30–60 minutes at approximately 4 degrees centigrade.

The media is removed and the virus is re-suspended in E-MEM test medium outlined below. The virus aliquot may be stored in liquid nitrogen until use or if processed on the day of testing, refrigerated until use in the assay. Immediately prior to testing, the stock virus is titered by 10-fold serial dilution and inoculated in quadruplicate into H1-HeLa cells (also from ATCC catalogue No. CRL-1958) to determine the input virus titer used in the tests.

Cell Cultures

The cells used to determine virucidal activity in this procedure are H1-HeLa cells (also from ATCC Catalogue No. CRL-1958). The medium used to grow the H1-HeLa cells is E-MEM supplemented with 10% FBS and 1% PSG. E-MEM is Minimum Essential Medium (with Earle's salts, non-essential amino acids and without L-glutamine) obtained from Life Technology, Inc. Rockville, Md. (Gibco BRL catalogue No. 10370-021); FBS is Fetal Bovine Serum obtained from Life Technology, Inc. Rockville, Md. (Gibco BRL catalogue No. 16140-071); and PSG is penicillin-streptamine-glutamine obtained from Life Technology, Inc. Rockville, Md. (Gibco BRL catalogue No. 10378-016).

Cultures are maintained and used as monolayers in growth flasks at 36–38 degrees centigrade in a humidified atmosphere of 5%–7% $CO_2$.

Test Medium

The test medium is E-MEM supplemented with 10% Bovine Mucin (Sigma Aldrich Cat. No. M-4503) and 1% PSG. E-MEM is Minimum Essential Medium (with Earle's salts, non-essential amino acids and without L-glutamine) obtained from Life Technology, Inc. Rockville, Md. (Gibco BRL catalogue No. 10370-021); and PSG is penicillin-streptamine-glutamine obtained from Life Technology, Inc. Rockville, Md. (Gibco BRL catalogue No. 10378-016).

Elution Media

The elution media is E-MEM with 1% PSG. E-MEM is Minimum Essential Medium (with Earle's salts, non-essential amino acids and without L-glutamine) obtained from Life Technology, Inc. Rockville, Md. (Gibco BRL catalogue No. 10370-021); and PSG is penicillin-streptamine-glutamine obtained from Life Technology, Inc. Rockville, Md. (Gibco BRL catalogue No. 10378-016).

METHOD

Preparation of Tissue Product

Samples of the tissue product to be tested are cut into 56±0.5 mm circular discs. The treated tissue discs containing antiviral compositions are utilized in the test and cytotoxicity control parameters. Control tissue discs which do not contain antiviral compositions are included for the positive virus control. The control disc is from the same lot of paper used to prepare the antiviral tissue paper.

Preparation of the Buchner Funnel Filtration Device

Using sterile technique, a pre-weighed disc of tissue paper of varying plies (depending on the tissue product tested) treated with virucide is placed in the bottom portion of each of two Buchner funnels. These will be used for one test replicate and one cytotoxicity control replicate. A disc of pre-weighed untreated tissue will be placed in one 56 millimeter Buchner funnel (Model No. 60240, available from Coors of Golden, Colo.) for use as the positive control.

Using sterile technique, a sterile test tube is inserted into a 250 milliliter filter flask so that the top of the tube rests against the neck of the flask. A rubber stopper is secured onto the outlet stem of the Buchner funnel. The funnel device is placed tightly into the opening of the filtration flask. The outlet stem of the Buchner funnel device is placed tightly into the opening of the filtration flask. The outlet stem of the Buchner funnel is lined up with the opening of the test tube to ensure that anything eluted from the Buchner funnel will be collected in the test tube. One end of a vacuum pump hose is connected to the side arm of the flask.

Treatment With Virus Suspension

An aliquot (500 microliters) of stock virus suspended in E-MEM supplemented with 10% Bovine Mucin (Sigma Aldrich Cat. No. M-4503) and 1% PSG is dispensed directly onto the center of the treated tissue discs using a calibrated pipetter. The virus aliquot is allowed to contact the tissue for exactly one (1) minute at room temperature and then immediately collected from the tissue by dispensing 3 milliliters of elution media onto the center region of the disc using a calibrated pipette and immediately applying vacuum suction.

The vacuum suction is applied for 15 seconds while lightly rocking the flask to release any volume caught in the capillaries of the Buchner funnel. The collected virus aliquot in the test tube ($10^{-1}$ dilution) is thoroughly mixed using a vortex mixer, titered by 10-fold serial dilutions (0.3 ml+2.7 ml Elution media) and assayed for the presence of virus. The tissue is removed from the Buchner funnel and a final weight is recorded.

Treatment of Virus Control (Positive Control)

An aliquot (500 microliters) of stock virus suspended in E-MEM supplemented with 10% FBS and 1% PSG is dispensed directly onto the center of the un-treated (control) tissue disc using a calibrated pipettor. The virus aliquot is allowed to contact the tissue for exactly one (1) minute at room temperature and then immediately collected from the tissue by dispensing 3 milliliters of E-MEM onto the center region of the disc using a calibrated pipette and immediately applying vacuum suction.

The vacuum suction is applied for 15 seconds while lightly rocking the flask to release any volume caught in the capillaries of the Buchner funnel. The collected virus aliquot is titered as described above. The average virus control titer will be used as a baseline to compare the log reduction of each test parameter following exposure to the products. The tissue is removed from the Buchner funnel and a final weight is recorded.

Infectivity Results

Quantitation of the viral activity of the various filtrates and stock virus is performed by inoculation of each dilution into the appropriate cell cultures in quadruplicate. The end point of a virucidal test for a given tissue is that dilution of virus which infects or is calculated to infect only one of two inoculation wells. This number is defined as the tissue culture infectivity dose or $TCID_{50}$. The results of the virucidal efficacy of a given tissue are given as the "log difference" or percent reduction between the common log of the $TCID_{50}$ result of the treated sample and the $TCID_{50}$ of the untreated sample.

The virucidal efficacy of a sample may be derived from the "log difference" in the following manner:

Virucidal Efficacy (in percent)=$(A-B)/A*100$

Where:

$A=TCID_{50}$ (units/ml) from the untreated tissue sample
$B=TCID_{50}$ (units/ml) from the treated tissue sample
Example Calculation:
$A=10^6$ units/ml
$B=10^2$ units/ml Viral efficacy=$(10^6-10^2)/10^6*100=99.99\%$ The procedure outlined above conforms to standard microbiological assay techniques and yields reliable and reproducible results within the limits of variability associated with such biological experiments.

EXAMPLES

Table 1 below indicates the virucidal efficacy of virucidal tissue made according to the present invention. Each of these samples was produced via slot extrusion of the virucidal composition onto the fabric side of a single ply of Puffs® Advanced Extra Strength tissue substrate. Each treated substrate was then combined into a 2-ply product wherein the fabric side of each treated ply was placed in a face-to-face relationship with one another such that the untreated side of each ply was facing outwardly (i.e.; wire side out). The virucidal efficacy of each tissue sample was then tested according to the Virucidal Assay Procedure described above. As used herein "fabric side" refers to that side of the tissue sheet which was not in contact with the foraminous surface of the paper machine. As used herein "wire side" refers to that side of the tissue sheet which was in contact with the foraminous surface of the paper machine.

Preparation of the virucidal composition used for each tissue sample in Table 1 is described below:

Tissue Sample 1

The virucidal composition for Tissue Sample 1 was made by mixing in Pidolidone® (pyrrolidone carboxylic acid commercially available from UCIB of France, distributed by Barnet Products Corporation of Englewood Cliffs, N.J.) with distilled water via a shaft mixer and heating the mixture to 170° F. (i.e.; 77° C.) to produce a 70% by weight solution of aqueous Pyrrolidone Carboxylic acid.

The pH of the solution was then increased to 2.5 by adding 50% (weight/weight) sodium hydroxide solution to help prevent acid induced corrosion of the stainless steel application equipment. The solution was then further heated to 180° F. (i.e.; 82° C.) and extruded onto the fabric side of a single ply of Puffs® Advanced Extra Strength tissue substrate. The addition rate of the virucidal composition was controlled to produce about a 10% by weight add-on of pyrollidone carboxylic acid to dry tissue.

Tissue Sample 2

The virucidal composition for Tissue Sample 2 was made according to the same procedure utilized for Tissue Sample 1. The only difference was in the add-on level for Tissue Sample 2 whereby the virucidal composition was controlled to produce about a 5% by weight add-on of pyrollidone carboxylic acid to dry tissue.

Tissue Sample 3

The virucidal composition for Tissue Sample 3 was made by heating distilled water to 170° F. (i.e.; 77° C.) and thereafter combining in Pidolidone® (pyrrolidone carboxylic acid commercially available from UCIB of France, distributed by Barnet Products Corporation of Englewood Cliffs, N.J.) and cupric sulfate pentahydrate (Lot 4752 T05611 commercially available from Mallinckrodt of Paris, Ky.) with a shaft mixer to produce an aqueous solution containing 50% by weight pyrollidone carboxylic acid and 5% by weight cupric sulfate.

The pH of the solution was then increased to 2.5 by adding 50% (weight/weight) sodium hydroxide solution to help prevent acid induced corrosion of the stainless steel application equipment. The solution was then further heated to 180° F. (i.e.; 82° C.) and extruded onto the fabric side of a single ply of Puffs® Advanced Extra Strength tissue substrate. The addition rate of the virucidal composition was controlled to produce about a 10% by weight add-on of pyrollidone carboxylic acid and about a 1% add-on of cupric sulfate to dry tissue.

Tissue Sample 4

The virucidal composition for Tissue Sample 4 was made according to the same procedure utilized for Tissue Sample 3. The only difference was in the add-on level for Tissue Sample 4 whereby the virucidal composition was controlled to produce about a 5% by weight add-on of pyrollidone carboxylic acid and about a 0.5% add-on of cupric sulfate to dry tissue.

Tissue Sample 5

The virucidal composition for Tissue Sample 5 was made according to the same procedure utilized for Tissue Sample 3. The only difference was in the add-on level for Tissue Sample 5 whereby the virucidal composition was controlled to produce about a 2% by weight add-on of pyrollidone carboxylic acid and about a 0.2% add-on of cupric sulfate to dry tissue.

Tissue Sample 6

The virucidal composition for Tissue Sample 6 was made by heating distilled water to 170° F. (i.e.; 77° C.) and thereafter combining in sequence Pidolidone® (pyrrolidone carboxylic acid commercially available from UCIB of France, distributed by Barnet Products Corporation of Englewood Cliffs, N.J.), 50% sodium hydroxide for pH adjustment to 2.5, and Tomadol 25-12 (commercially available from Tomah Products Incorporated of Reserve, La.) with a shaft mixer to produce a 70% by weight pyrrolidone carboxylic acid and 0.5% by weight Tomadol 25-12 solution.

The solution was then further heated to 180° F. (i.e.; 82° C.) and extruded onto the fabric side of a single ply of Puffs® Advanced Extra Strength tissue substrate. The addition rate of the virucidal composition was controlled to produce about a 10% by weight add-on of pyrollidone carboxylic acid and about a 0.07% by weight add-on of Tomadol 25-12 to dry tissue.

Tissue Sample 7

The virucidal composition for Tissue Sample 7 was made by heating distilled water to 170° F. (i.e.; 77° C.) and thereafter combining in sequence Pidolidone® (pyrrolidone carboxylic acid commercially available from UCIB of France, distributed by Barnet Products Corporation of Englewood Cliffs, N.J.), cupric sulfate pentahydrate (commercially available from Mallinckrodt of Paris, Ky.), 50% sodium hydroxide for pH adjustment to 2.5, Tomadol 25-12 (commercially available from Tomah Products Incorporated of Reserve, La.), and CM 849 (polydimethylsiloxane emulsion having an active silicone level of 42.5%, commercially available from General Electric of Fairfield, Conn.) with a shaft mixer to produce a 50% by weight pyrrolidone carboxylic acid, 5% by weight cupric sulfate, 0.5% by weight Tomadol 25-12, and 2.38% by weight polydimethylsiloxane emulsion (1% active silicone) composition.

The composition was then further heated to 180° F. (i.e.; 82° C.) and extruded onto the fabric side of a single ply of Puffs® Advanced Extra Strength tissue substrate. The addition rate of the virucidal composition was controlled to produce about a 10% by weight add-on of pyrollidone carboxylic acid, about a 1% by weight add-on of cupric sulfate, about a 0.1% by weight add-on of Tomadol 25-12, and about a 0.47% add-on of active silicone on dry tissue.

Tissue Sample 8

The virucidal composition for Tissue Sample 8 was made according to the same procedure utilized for Tissue Sample 7. The only difference was in the add-on level for Tissue Sample 8 whereby the virucidal composition was controlled to produce about a 5% by weight add-on of pyrollidone carboxylic acid, about a 0.5% add-on of cupric sulfate, about a 0.05% by weight add-on of Tomadol 25-12, and about a 0.24% add-on of active silicone on dry tissue.

TABLE 1

Virucidal efficacy of treated Puffs ® Advanced Extra Strength tissues against Rhinovirus 14 (Exposure time 1 minute)

| Tissue Sample No. | Virucidal Composition[a] | | | Additives[a] | | Virucidal Efficacy (%) |
|---|---|---|---|---|---|---|
| | PCA[c] (%) | CuPCA (%) | CuSO4 (%) | Tomadol 25-12 (%) | Silicone Emulsion[b] (%) | |
| 1 | 10 | — | — | — | — | 99.67 |
| 2 | 5 | — | — | — | — | 90.00 |
| 3 | 10 | 1 | — | — | — | 99.60 |
| 4 | 5 | 0.5 | — | — | — | 93.19 |
| 5 | 2 | 0.2 | — | — | — | 95.36 |
| 6 | 10 | — | — | 0.07 | — | 93.91 |
| 7 | 10 | — | 1 | 0.1 | 0.47 | >99.97 |
| 8 | 5 | — | 0.5 | 0.05 | 0.24 | 95.36 |

[a]Figures are in % chemical addition on air dry tissue.
[b]Polydimethylsiloxane emulsion - CM 849 available from General Electric of Fairfield, Connecticut.
[c]Pyrrolidone Carboxylic Acid While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. An antiviral tissue product, said antiviral tissue product comprising:
   a) a fibrous ply;
   b) an antiviral composition wherein said antiviral composition comprises pyrrolidone carboxylic acid; and
   c) an "Easiness to Loosen in Water" test value of greater than about 100 seconds.

2. The antiviral tissue product of claim 1 wherein said pyrrolidone carboxylic acid comprises from about 0.05% to 50% by weight of said antiviral tissue product.

3. The antiviral tissue product of claim 1 further comprising a wet strength resin wherein said wet strength resin comprises from about 0.05% to 10% by weight of said antiviral tissue product.

4. The antiviral tissue product of claim 1 wherein said antiviral composition further comprises a metal salt.

5. The antiviral tissue product of claim 4 wherein said metal salt comprises from about 0.001% to 20% by weight of said antiviral composition and wherein said metal salt is copper pidolate, L-FER pidolate, cuprous sulfate, cupric sulfate, ferrous chloride, ferric chloride, cupric chloride, cuprous chloride, ferrous sulfate, ferric sulfate, or combinations thereof.

6. The antiviral tissue product of claim 1 wherein said antiviral composition further comprises a surfactant.

7. The antiviral tissue product of claim 6 wherein said surfactant comprises from about 0.01% to 10% by weight of said antiviral composition and wherein said surfactant is nonionic, cationic, anionic, zwitterionic, amphoteric, or mixtures thereof.

8. The antiviral tissue product of claim 1 wherein said antiviral composition further comprises an optional organic acid.

9. The antiviral tissue product of claim 8 wherein said optional organic acid comprises from about 0.1% to 80% by weight of said antiviral composition and wherein said optional organic acid is citric acid, malic acid, lactic, glutaric acid, succinic acid, or mixtures thereof.

10. The antiviral tissue product of claim 1 wherein said antiviral tissue product further comprises a lotion.

11. The antiviral tissue product of claim 10 wherein said lotion comprises from about 0.01% to 40% by weight of said antiviral tissue product and wherein said lotion is polysiloxane.

12. The antiviral tissue product of claim 11 wherein said lotion further comprises an antiviral composition whereby said antiviral composition comprises from about 0.05% to 80% by weight of said lotion and wherein said antiviral composition is pyrrolidone carboxylic acid, citric acid, malic acid, lactic acid, glutaric acid, succinic acid, or mixtures thereof.

13. The antiviral tissue product of claim 12 wherein said antiviral composition of said lotion is pyrrolidone carboxylic acid.

14. The antiviral tissue product of claim 1 further comprising a moisture barrier.

15. The antiviral tissue product of claim 14 wherein said moisture barrier further comprises an antiviral composition.

16. An antiviral tissue product, said antiviral tissue product comprising:
   a first fibrous ply having a first surface and a second surface whereby said second surface is oppositely disposed with respect to said first surface, said first surface including an antiviral composition wherein said antiviral composition is pyrrolidone carboxylic acid; said second surface including an antiviral composition wherein said antiviral composition is citric acid, salicylic acid, malic acid, glutaric acid, succinic acid, or mixtures thereof.

17. The antiviral tissue product of claim 16, further comprising:
   a second fibrous ply joined in a face to face relationship with said first fibrous ply, said second fibrous ply having a first surface and a second surface whereby said second surface is oppositely disposed with respect to said first surface, and whereby said second surface of said second fibrous ply faces toward said second surface of said first fibrous ply.

18. The antiviral tissue product of claim 17 wherein said first surface of said second fibrous ply further comprises a lotion wherein said lotion comprises from about 0.01% to 40% by weight of said second fibrous ply.

19. The antiviral tissue product of claim 18 wherein said lotion further comprises an antiviral composition whereby said antiviral composition comprises from about 0.05% to 80% by weight of said lotion and wherein said antiviral composition is pyrrolidone carboxylic acid, citric acid, malic acid, lactic acid, glutaric acid, succinic acid, or mixtures thereof.

20. The antiviral tissue product of claim 17 further comprising a moisture barrier wherein said moisture barrier is juxtaposed between said second surface of said first fibrous ply and said second surface of said second fibrous ply.

21. The antiviral tissue product of claim 17 further comprising a moisture barrier wherein said moisture barrier is impregnated into said second fibrous ply.

22. The antiviral tissue product of claim 16 further comprising a third fibrous ply joined in a face to face relationship with said first and second fibrous plies, said third fibrous ply having a first surface and a second surface whereby said second surface is oppositely disposed with respect to said first surface, and whereby said second surface of said third fibrous ply faces toward said second surface of said second fibrous ply.

23. The antiviral tissue product of claim 22 wherein said first surface of said third fibrous ply further comprises a lotion.

24. The antiviral tissue product of claim 23 wherein said lotion further comprises an antiviral composition whereby said antiviral composition comprises from about 0.05% to 80% by weight of said lotion and wherein said antiviral composition is pyrrolidone carboxylic acid, citric acid, malic acid, lactic acid, glutaric acid, succinic acid, or mixtures thereof.

25. The antiviral tissue product of claim 22 wherein said second surface of said third fibrous ply further comprises an antiviral composition wherein said antiviral composition is pyrrolidone carboxylic acid, citric acid, salicylic acid, malic acid, lactic acid, glutaric acid, succinic acid, or mixtures thereof.

26. The antiviral tissue product of claim 22 wherein said first surface of said third fibrous ply further comprises an antiviral composition wherein said antiviral composition is pyrrolidone carboxylic acid, citric acid, salicylic acid, malic acid, lactic acid, glutaric acid, succinic acid, or mixtures thereof.

27. The antiviral tissue product of claim 17 wherein said antiviral composition of said first surface of said first fibrous ply further comprises a metal salt.

28. A process for making an antiviral tissue product, said process comprising the steps of:
a) providing a first fibrous ply having a first surface and a second surface whereby said second surface is oppositely disposed with respect to said first surface;
b) adding an antiviral composition to said first surface of said first fibrous ply wherein said antiviral composition is pyrrolidone carboxylic acid;
c) providing a second fibrous ply joined in a face to face relationship with said first fibrous ply, said second fibrous ply having a first surface and a second surface whereby said second surface is oppositely disposed with respect to said first surface, and whereby said second surface of said second fibrous ply faces toward said second surface of said first fibrous ply.

29. The process of claim 28 wherein said antiviral composition is added discretely to said first surface of said first fibrous ply.

30. The process of claim 28 further comprising adding a lotion to said first surface of said second fibrous ply.

31. The process of claim 30 wherein said lotion is added discretely to said first surface of said second fibrous ply.

32. The process of claim 28 further comprising adding a third fibrous ply.

33. The process of claim 32 further comprising adding a fourth fibrous ply.

34. The process of claim 28 wherein said antiviral tissue product has an "Easiness to Loosen in Water" test value of greater than about 100 seconds.

35. The process of claim 28 further comprising adding a wet strength resin to said first fibrous ply.

\* \* \* \* \*